(12) United States Patent
Moran et al.

(10) Patent No.: US 7,715,908 B2
(45) Date of Patent: May 11, 2010

(54) SYSTEMS AND METHODS FOR A HOT-SWAPPABLE CATHETER INPUT MODULE

(75) Inventors: Patrick Thomas Moran, New Berlin, WI (US); Rodger F. Schmit, West Bend, WI (US); Daniel Richard Schneidewend, Menomonee Falls, WI (US)

(73) Assignee: General Electric Company, Schenectady, NY (US)

( * ) Notice: Subject to any disclaimer, the term of this patent is extended or adjusted under 35 U.S.C. 154(b) by 859 days.

(21) Appl. No.: 11/550,057

(22) Filed: Oct. 17, 2006

(65) Prior Publication Data

US 2008/0169925 A1 Jul. 17, 2008

(51) Int. Cl.
*A61B 5/0428* (2006.01)
(52) U.S. Cl. ...................................... 600/522
(58) Field of Classification Search ................ 600/522
See application file for complete search history.

(56) References Cited

U.S. PATENT DOCUMENTS 5,607,462 A * 3/1997 Imran ......................... 607/122
2001/0021799 A1* 9/2001 Ohlsson ...................... 600/300

OTHER PUBLICATIONS

Siemens—Axiom Sensis: http://cardiology.usa.siemens.com/products-and-it-systems/cardiology-products/interventional-cardiology/reporting-software/sensis.aspx.
Philips—EP Workmate: http://www.medical.philips.com/main/products/cardiovascular/cv_homepage_solutions_electrophysiologist.html.
Witt/Philips—Series IV: http://www.medical.philips.com/main/products/cardiovascular/products/ipc/series_iv/.
Mennen—Horizon SE: http://www.mennenmedical.com/len/agallery%20presentation/c1470/10515.php.
Camtronics—PhysioLab: http://www.camtronics.com/heartsuite/?inc=heartsuitehemo.htm.
EP Med EP Workmate: http://www.epmedsystems.com/products.html.
Bard Labsystem Pro: http://www.bardnordic.com/main/product.asp?sectionTypeId=2&sectionId=16&productId=193.

* cited by examiner

*Primary Examiner*—Kennedy J Schaetzle
(74) *Attorney, Agent, or Firm*—McAndrews, Held & Malloy, Ltd.; Peter J. Vogel; Michael A. Dellapenna

(57) ABSTRACT

Certain embodiments of the present invention provide a catheter monitoring system including a catheter input module (CIM) adapted to be connected to at least one catheter, an amplifier base, and a host adapted to process data from the amplifier base. The CIM is adapted to be connected to an amplifier base during a study. The amplifier base is adapted to receive data from the CIM when the CIM is connected to the amplifier base.

18 Claims, 4 Drawing Sheets

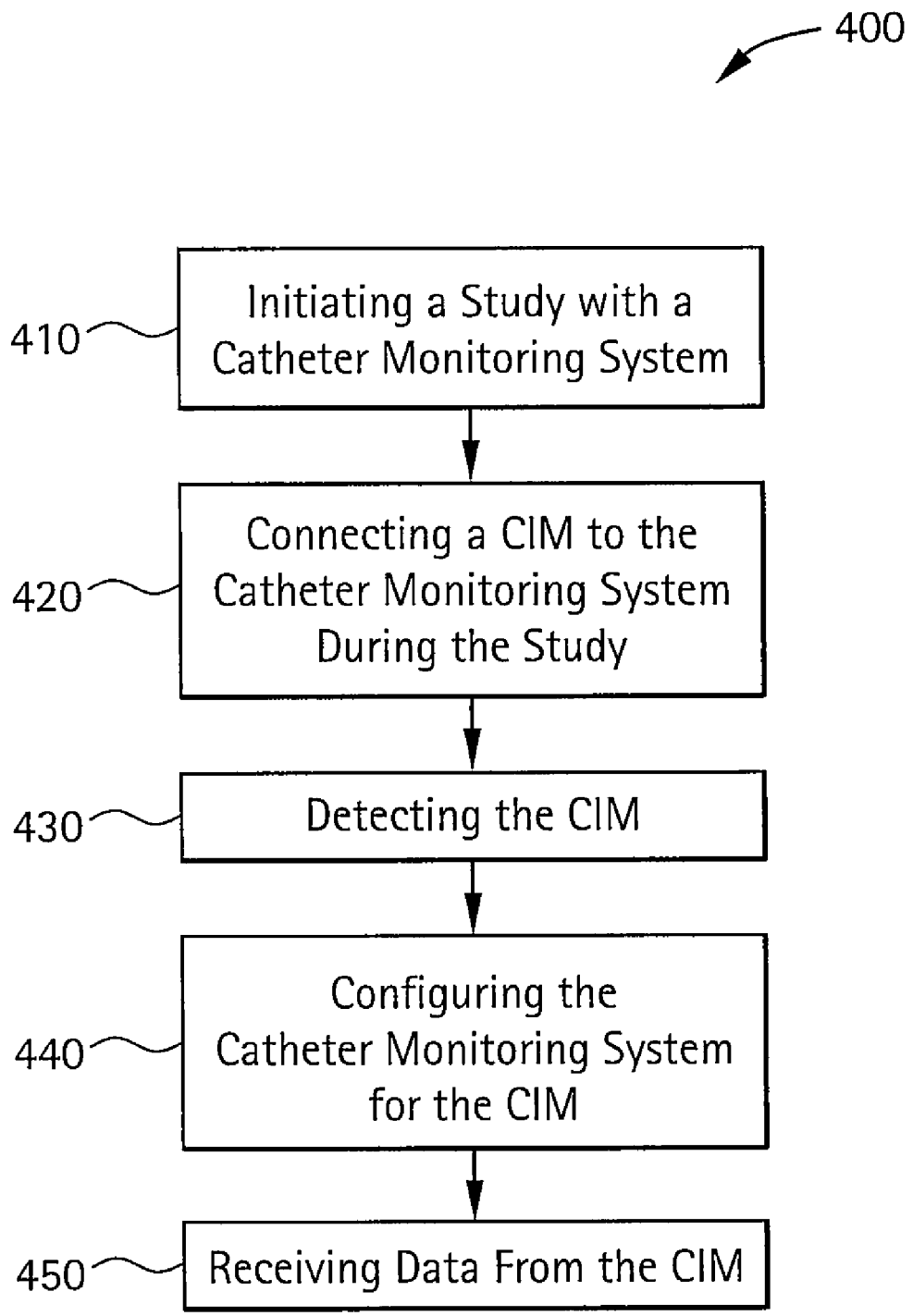

SYSTEMS AND METHODS FOR A HOT-SWAPPABLE CATHETER INPUT MODULE

BACKGROUND OF THE INVENTION

The present invention generally relates to catheter monitoring. In particular, the present invention relates to systems and methods for a hot-swappable catheter input module.

The normal pumping of the heart results from the ordered contraction of the muscles of the heart, the myocardium. When the myocardium is electrically stimulated, it contracts. The sinoatrial node (SA node) generates an electrical impulse that is propagated to the myocardium. Typically, the SA node spontaneously generates the electrical impulse. Certain problems may occur when the electrical impulse is generated and/or propagates incorrectly.

An electrophysiology (EP) study may include one or more tests performed to acquire data about the electrical signals in the heart. An EP study is performed by placing one or more catheters into a patient's heart. The catheters monitor the electrical signals in the heart. A catheter may include one or more leads for relaying the monitored signals to a catheter monitoring system such as an EP laboratory system. In some situations, a catheter may be used to stimulate the heart by introducing electrical impulses in an EP study.

For example, to perform an EP study, three intracardiac (IC) catheters may be placed into a patient's heart to monitor the electrical signals as they travel through the heart and cross the three catheters. The catheters may be connected to input ports on a catheter input module (CIM) that is part of the monitoring system. Each catheter may have one or more data channels. A data channel includes a signal electrode and a reference electrode. The reference electrode may come from a lead in the catheter or from an auxiliary or external reference, for example.

Current systems utilize an amplifier to receive and amplify input from IC catheters. The number of inputs available for the IC catheters may be fixed based on the amplifier model purchased. Thus, when additional catheter inputs are desired, a user must replace the entire amplifier with a different model, incurring additional cost and system downtime. In other current systems, the amplifier may utilize one or more CIMs. In such systems, when additional catheter inputs are desired, the catheter monitoring system must be powered down and opened up for the new CIM hardware to be installed.

As discussed above, current systems do not support the addition of additional catheter inputs to the hardware during a study. However, the number of catheter inputs needed during a study can change. For example, during a study a healthcare practitioner may determine an additional catheter is desired to be included in the study. As another example, at the beginning of a study, only a subset of the leads from a catheter may be used. During the study, the healthcare provider may decide to utilize additional leads. If additional catheter inputs are not available when desired during the study, the study will have to be closed before the amplifier can be replaced or powered down so additional CIMs can be added.

In addition, when adding a new CIM, there is a possibility that the CIM will be damaged if the power is left on by mistake. That is, a user may accidentally attempt to add a CIM while the catheter monitoring system is still powered on. This may result in permanent damage to the CIM and/or the catheter monitoring system.

Thus, there is a need for a hot-swappable catheter input module.

BRIEF SUMMARY OF THE INVENTION

Certain embodiments of the present invention provide a catheter monitoring system including a catheter input module (CIM) adapted to be connected to at least one catheter, an amplifier base, and a host adapted to process data from the amplifier base. The CIM is adapted to be connected to an amplifier base during a study. The amplifier base is adapted to receive data from the CIM when the CIM is connected to the amplifier base. The amplifier base adapted to communicate the received data to the host. The host is adapted to display the data when the CIM is connected Certain embodiments of the present invention provide a catheter input module including a catheter input port adapted to receive input from at least one catheter and a data port adapted to be connected to a catheter monitoring system. The data port is adapted to be connected to the system during a study. The data port is adapted to communicate the received input to the system.

Certain embodiments of the present invention provide a method of acquiring data for an electrophysiological study including initiating an electrophysiological study with a catheter monitoring system, connecting a hot-swappable catheter input module (CIM) to the catheter monitoring system during the study, and receiving data from the CIM.

BRIEF DESCRIPTION OF SEVERAL VIEWS OF THE DRAWINGS

FIG. 4 illustrates a flow diagram for a method for medical navigation according to an embodiment of the present invention.

Figure 1:
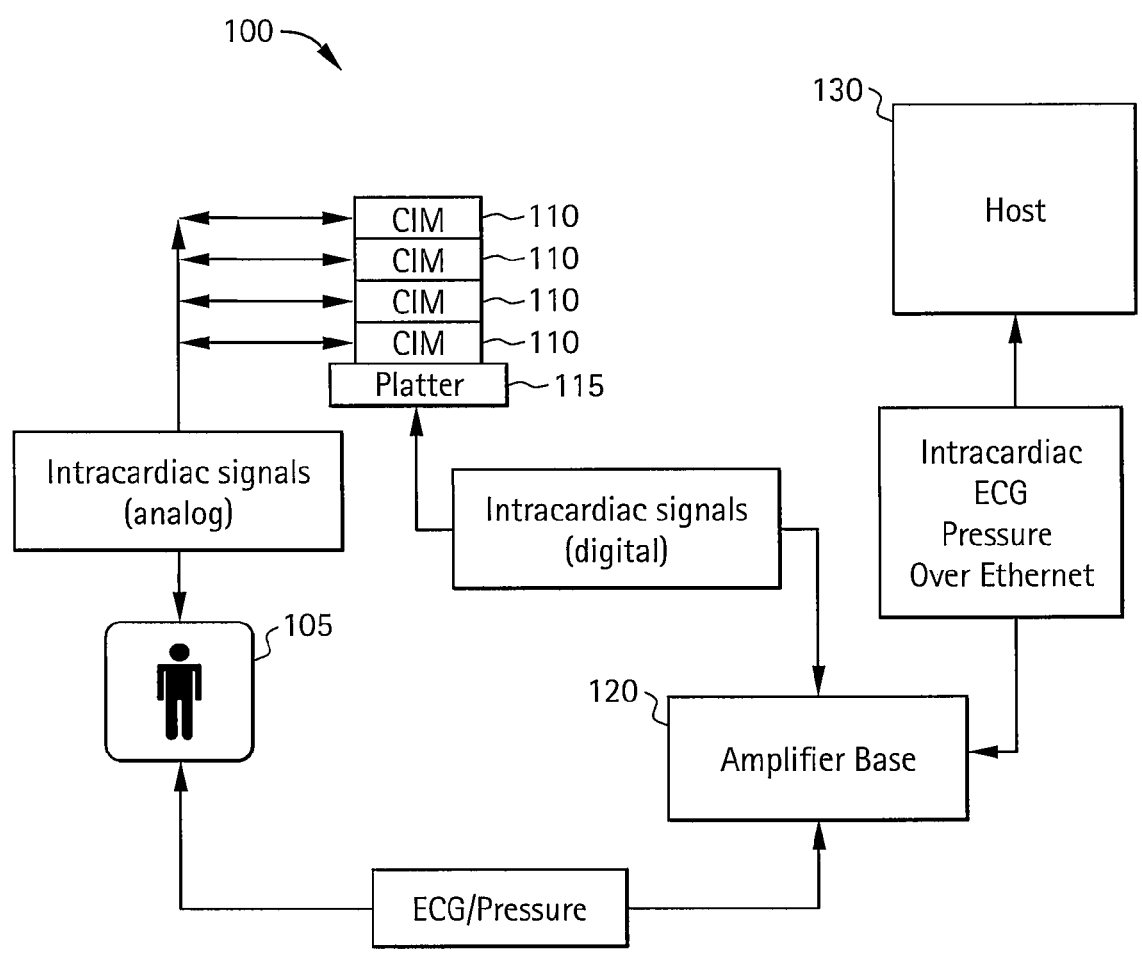
FIG. 1 illustrates a catheter monitoring system according to an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a catheter monitoring system 100 according to an embodiment of the present invention. The catheter monitoring system 100 includes one or more catheter input modules (CIMs) 110, an amplifier base 120, and a host 130. The CIMs 110 are in communication with the amplifier base 120. The amplifier base 120 is in communication with the host 130. In certain embodiments, the CIMs 110 may be coupled to the amplifier base 120 through a platter 115.

In operation, one or more catheters are inserted into a patient 105. The catheters may be intracardiac (IC) catheters, for example. The catheters may be placed into various locations in the heart of the patient 105, for example. For example, catheters may be inserted as part of an EP study.

A catheter sends signal data to the amplifier base 120 through one or more CIMs 110. The catheters may include one or more electrodes with leads connecting to input ports on a CIM 110, for example. The leads may connect to a socket, plug, and/or one or more pins of a catheter input port, for example.

Each catheter may have one or more data channels. A data channel includes a signal electrode and a reference electrode. The reference electrode may come from a lead in the catheter or from an auxiliary or external reference, for example. Multiple channels may share a reference electrode. For example, an electrode from the catheter may serve as a reference for several other leads to form multiple channels. As another example, an external reference signal, such as a surface electrode, may be utilized as the reference for one or more channels.

A CIM 110 receives the signal data from a catheter through a catheter port in the CIM 110. For example, one or more leads from the catheter may be plugged into the catheter port in the CIM 110 The catheter port may include a socket, plug, and/or one or more pins, for example The CIM 110 communicates the signal data from the catheter to the amplifier base 120 through a data port in the CIM 110. For example, the data port of the CIM may be connected to the amplifier base 120 by a cable. In certain embodiments, the cable may be daisy-chained with other CIMs 110. In certain embodiments, a cable may be directly connected from each CIM 110 to the amplifier base 120.

As mentioned above, in certain embodiments, a CIM 110 is connected to the amplifier base 120 through a platter 115. For example, a cable may be connected to the data port of a first CIM 110, daisy-chained to the data port of a second CIM 110, and then connected to a platter 115. The platter 115 may then include a connection such as a cable to the amplifier base 120. In certain embodiments, the platter 115 is part of the amplifier base 120.

The amplifier base 120 is adapted to receive data from one or more CIMs 110. The amplifier base 120, as described above, may receive the data from the one or more CIMs 110 through the platter 115, for example.

The amplifier base 120 may receive data from inputs other than the CIMs 110. For example, the amplifier base 120 may receive data from a surface lead As another example, the amplifier base 120 may receive data from a blood pressure monitor.

The amplifier base 120 may amplify or process the received data. For example, the amplifier base 120 may increase the gain on the signal data from a CIM 110. As another example, the amplifier base 120 may filter noise from the signal data from a CIM 110.

After receiving the data, and any processing, the amplifier base 120 communicates the data to the host 130. The amplifier base 120 may communicate the received data as a digital signal. Alternatively, the amplifier base 120 may communicate the received data as an analog signal. The amplifier base 120 may communicate the data to the host 130 over a wired and/or wireless connection, for example. For example, the amplifier base 120 may communicate the data to the host 130 using the Ethernet protocol. As another example, the amplifier base 120 may communicate the data to the host 130 using a special-purpose communication protocol. The special-purpose protocol may include slots for some predetermined number of data sources. Each slot may include data from the source or a value indicating the source is not present or the data is not valid, for example.

The host 130 receives data from the amplifier base 120. The host 130 is adapted to present the data. The host may display the data to a user, for example. The host 130 is adapted to save the data. The host may save the data to a file or an information management system, for example.

The host 130 may display and/or save the data based on a configuration, for example. The configuration may be user-defined. For example, the configuration may indicate that data from a particular catheter, signal, or channel is to be displayed at a certain location on the screen or in a certain color. As another example, the configuration may indicate that a filter is to be applied to the data.

A user may make a configuration for signals that are not currently being received. For example, a user may provide configurations for 18 channels, while only 8 are in use. When a new channel is added, the host will then utilize the appropriate configuration for that new channel. When no data is received for a channel, the channel may not be displayed. When data starts being received at the host 130 for the channel, the channel may then be displayed and processed based at least in part on the configuration.

The host 130 may process received data. The data may be processed before it is presented and/or saved, for example. As mentioned above, the host 130 may process received data based at least in part on a configuration. For example, the host 130 may apply a low pass filter to the data. The low pass filter may have a range from 100 to 1000 Hz, for example. As another example, the host 130 may apply a high pass filter to the data. The high pass filter may have a range from 0.05 to 30 Hz, for example. The type of filtering and the ranges may be configured by a user, for example.

As discussed above, it is desirable to add new CIMs 110 to the catheter monitoring system 100 during a study. Certain embodiments of the present invention include hot-swappable CIMs 110. That is, the CIM 110 is adapted to be connected during a study, without powering down the system 100. In other words, the CIM 110 is adapted to be connected when the system 100 is powered on. For example, the CIM 110 may be connected to the amplifier base 120 during the study. As another example, the CIM 110 may be connected to the platter 115 during the study. In certain embodiments of the present invention, the CIM 110 is adapted to be connected to the system 100 during the normal operating mode of the system 100. That is, the system 100 does not need to be powered down or placed into a suspended mode for the CIM 110 to be connected or disconnected.

In addition, according to certain embodiments of the present invention, a CIM 110 may be removed from the system 100 during a study. The CIM 110 may be disconnected from the amplifier base 120 during a study. The CIM 110 may be disconnected without powering down the system 100 and/or the amplifier base 120. The CIM 110 may be disconnected during the normal operating mode of the system 100.

In certain embodiments, the circuits of the CIM 110 are protected against excessive current draw. In certain embodiments, 12 Volt input power of the CIM 110 is protected with a 1 Amp rated PolySwitch resettable over-current protection device, such as a Raychem SMD 110. In certain embodiments, the +5 Volt and +3.3 Volt internal power supplies of the CIM 110 are protected with a 3 Amp rated non-latching output over-current protection built into the power modules. For example, a Tyco AXA003A0X-5RZ may be utilized.

In certain embodiments, the circuits of the CIM 110 are protected against electrostatic discharge. In certain embodiments, +12 Volt input power, +5 Volt and +3.3 Volt internal power supplies are protected from over-voltage with transient suppressor diodes. For example, On Semiconductor 1SMB13AT3 and/or On Semiconductor 1SMB5.0AT3 may be used. In certain embodiments, analog signals are protected from over-voltage with switching diodes such as National Electronics MMBD1503A, connected to +5 Volt and ground power rails. In certain embodiments, RS-485 digital communication signals are protected by RS-485 digital transceivers, such as Texas Instruments 75HVD10D, which have built-in electrostatic discharge and short circuit protection.

In certain embodiments, the portion of the data port of the CIM 110 that communicates data signals may be physically offset from the portion of the data port of the CIM 110 that provides power to the CIM 110. Thus, in the normal action of using the port, the signal connections may be made before the power connections. This may prevent damage to the hardware of the CIM 110 and/or the system 100 during connection and/or disconnection of the CIM 110.

The amplifier base 120 is adapted to detect the connection of a new CIM 110 during a study. The amplifier base 120 may detect the connection of the CIM 110 by the availability of data, for example. As another example, the amplifier base 120 may detect the connection of the CIM 110 based at least in part on the flow of power. The amplifier base 120 is adapted to configure the new CIM 110 when it is connected. The amplifier base 120 is adapted to communicate data received from the new CIM 110 to the host 130.

As discussed above, the host 130 is adapted to process the new data received during a study. For example, the host 130 may display the new data when it is received based at least in part on a user-defined configuration. As another example, the host 130 may begin filtering the data channels received from the new CIM 110. As another example, the host 130 may begin saving the new data received from the CIM 110 when it is connected during a study.

Figure 2:
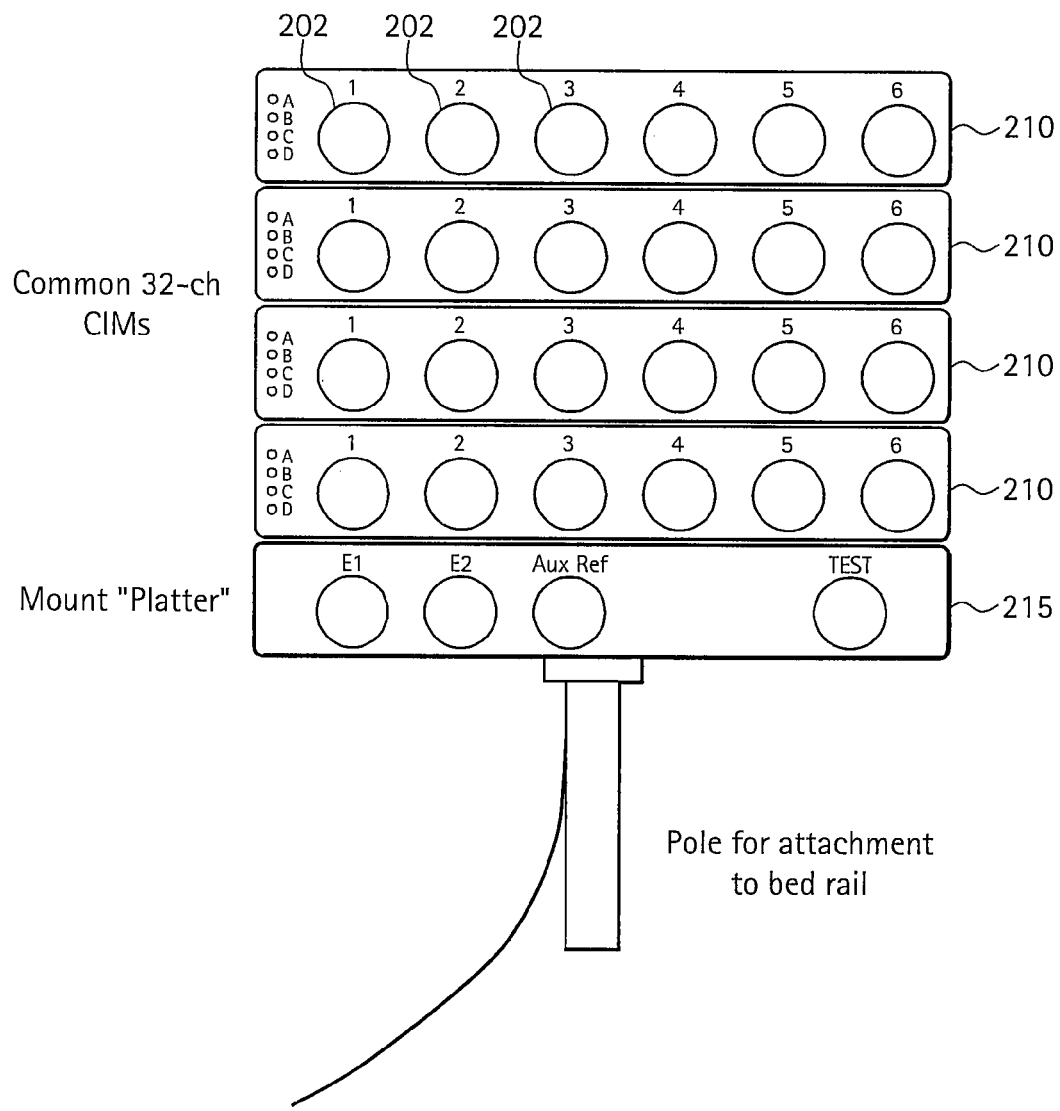
FIG. 2 illustrates a front view of four catheter input modules and a platter according to an embodiment of the present invention.

FIG. 2 illustrates a front view of four catheter input modules 210 and a platter 215 according to an embodiment of the present invention. The catheter input modules 210 may be similar to the CIMs 110, described above, for example. The platter 215 may be similar to the platter 115, described above, for example.

Each CIM 210 includes one or more catheter ports 202. As discussed above, a CIM 210 may receive signal data from a catheter through a catheter port 202. For example, one or more leads from the catheter may be plugged into the catheter port 202 in one or more CIMs 210. The catheter port 202 may include a socket, plug, and/or one or more pins, for example.

In certain embodiments, the CIM 210 includes an indicator. The indicator may include a light, light-emitting diode (LED), and/or liquid crystal display (LCD), for example. The indicator may identify the CIM 210 to a user when the CIM 210 is connected to the catheter monitoring system. For example, a light may be illuminated when the CIM 210 is connected and configured by the catheter monitoring system during a study.

Figure 3:
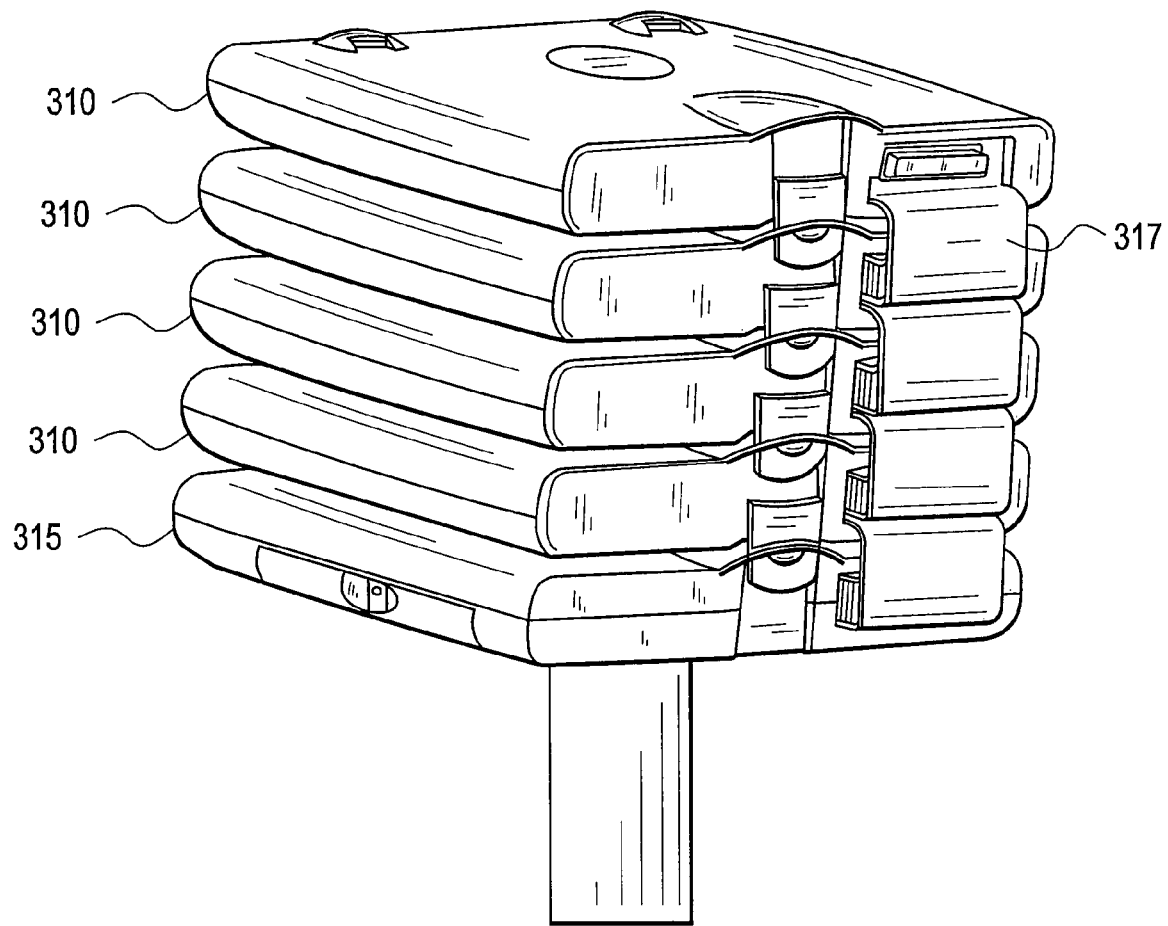
FIG. 3 illustrates a rear perspective view of four catheter input modules and a platter according to an embodiment of the present invention.

FIG. 3 illustrates a rear perspective view of four catheter input modules 310 and a platter 315 according to an embodiment of the present invention. The catheter input modules 310 may be similar to the CIMs 110 and/or the CIMs 210, described above, for example. The platter 315 may be similar to the platter 115 and/or the platter 215, described above, for example.

As illustrated in FIG. 3, a cable 317 is daisy-chained to each of the CIMs 310 in a manner similar to that described above. The cable 317 is connected to the data port of each CIM 310. In addition, the cable 317 connects the CIMs 310 to the platter 315. A data port may include a socket, plug, and/or one or more pins, for example.

The cable 317 communicates data between a CIM 310 and a catheter monitoring system. The catheter monitoring system may be similar to the catheter monitoring system 100, described above, for example. The cable 317 communicates the data from a CIM 310 through the platter 315.

The components, elements, and/or functionality of catheter monitoring system 100 may be implemented alone or in combination in various forms in hardware, firmware, and/or as a set of instructions in software, for example. Certain embodiments may be provided as a set of instructions residing on a computer-readable medium, such as a memory or hard disk, for execution on a general purpose computer or other processing device, such as, for example, a PACS workstation or one or more dedicated processors.

FIG. 4 illustrates a flow diagram for a method 400 for medical navigation according to an embodiment of the present invention. The method 500 includes the following steps, which will be described below in more detail. At step 410, a study is initiated with a catheter monitoring system. At step 420, a catheter input module (CIM) is connected to the catheter monitoring system during the study. At step 430, the CIM is detected. At step 440, the catheter monitoring system is configured for the CIM. At step 450, data is received from the CIM. The method 400 is described with reference to elements of systems described above, but it should be understood that other implementations are possible.

At step 410, a study is initiated with a catheter monitoring system. The catheter monitoring system may be similar to the catheter monitoring system 100, described above, for example. The study may be an EP study, for example.

At step 420, a catheter input module (CIM) is connected to the catheter monitoring system during the study. The catheter input module may be similar to the CIM 110, 210, and/or 310, described above, for example. The study may be the study initiated at step 410, described above, for example.

The CIM may be a hot-swappable CIM. That is, the CIM may be adapted to be connected during a study, without powering down the system. In other words, the CIM may be adapted to be connected when the system is powered on. For example, the CIM 110 may be connected to the amplifier base 120 during the study. As another example, the CIM 110 may be connected to the platter 115 during the study. In certain embodiments of the present invention, the CIM is adapted to connect to the system during the normal operating mode of the system. That is, the system does not need to be powered down or placed into a suspended mode for the CIM to be connected or disconnected.

In addition, according to certain embodiments of the present invention, the CIM may be removed from the system during a study. The CIM 110 may be disconnected from the amplifier base 120 during a study, for example. The CIM 110 may be disconnected without powering down the system 100 and/or the amplifier base 120, for example.

In certain embodiments, the circuits of the CIM are protected against excessive current draw. In certain embodiments, the circuits of the CIM are protected against electrostatic discharge. In certain embodiments, the portion of the data port of the CIM that communicates data signals may be offset from the portion of the data port of the CIM that provides power to the CIM. Thus, the signal connections may be made before the power connections.

At step 430, the CIM is detected. The CIM may be the CIM connected at step 420, described above, for example. The CIM may be detected by the catheter monitoring system, for example. The CIM may be detected by an amplifier base similar to the amplifier base 120, described above, for example.

The catheter monitoring system may detect the CIM by the presence of data at a port of the catheter monitoring system, for example. As another example, the catheter monitoring system may detect the connection of the CIM based at least in part on the flow of power.

At step 440, the catheter monitoring system is configured for the CIM. The catheter monitoring system may be configured based at least in part on a user-defined configuration for the CIM, for example. For example, when the new CIM is detected, the catheter monitoring system may begin processing, storing, and/or displaying the data from the new CIM. The processing, storing, and/or displaying of the data may be performed by the host of the catheter monitoring system. The host may be similar to the host 130, described above, for example. The catheter monitoring system may filter the received data, for example. As another example, the catheter monitoring system may display the received data in accordance with a configuration.

At step 450, data is received from the CIM. The data may be received at the amplifier base of the catheter monitoring system. The amplifier base may be similar to the amplifier base 120, described above, for example. The data may be received at the host of the catheter monitoring system. The host may be similar to the host 130, described above, for example.

One or more of the steps of the method 400 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Thus, certain embodiments of the present invention provide a hot-swappable catheter input module. Certain embodiments provide a technical effect of a hot-swappable catheter input module.

While the invention has been described with reference to certain embodiments, it will he understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A catheter monitoring system, the system including:
 a catheter input module (CIM) adapted to be connected to at least one catheter, wherein the CIM is adapted to be connected to an amplifier base during a study;
 the amplifier base adapted to receive data from the CIM when the CIM is connected to the amplifier base, the amplifier base adapted to communicate the received data to a host; and
 the host adapted to process data from the amplifier base, wherein the host is adapted to display the data when the CIM is connected and wherein the CIM is hot-swappable.

2. The system of claim 1, wherein the CIM is adapted to be connected to the amplifier base during a normal operating mode of the system.

3. The system of claim 1, wherein the CIM is adapted to be connected to the amplifier base when the system is powered on.

4. The system of claim 1, wherein the CIM is adapted to be disconnected from the amplifier base during the study.

5. The system of claim 1, wherein the CIM is configured such that a signal connection is made to the amplifier base before a power connection.

6. The system of claim 1, wherein the CIM is connected to the amplifier base using a platter.

7. The system of claim 1, wherein the amplifier base is adapted to detect the connection of the CIM, and wherein the amplifier base is adapted to configure the CIM when the connection is detected.

8. The system of claim 7, wherein the amplifier base is adapted to communicate the received data to a host after the CIM has been configured.

9. The system of claim 1, wherein the host is adapted to save data received when the CIM is connected.

10. The system of claim 1, wherein the host is adapted to allow a user to define a configuration for a CIM when the CIM is not connected to be used when the CIM is connected.

11. A catheter input module, the module including:
 a catheter input port adapted to receive input from at least one catheter; and
 a data port adapted to be connected to a catheter monitoring system, wherein the data port is adapted to be connected to the system during a study, and wherein the data port is adapted to communicate the received input to the system and wherein the data port is adapted to be hot-swappable.

12. The module of claim 11, wherein the data port is adapted to be connected to the catheter monitoring system during a normal operating mode of the system.

13. The module of claim 11, wherein the data port is adapted to be connected to the catheter monitoring system when the system is powered on.

14. The module of claim 11, wherein the data port is adapted to be connected to the catheter monitoring system before a power port.

15. The module of claim 11, wherein the data port is adapted to be disconnected from the catheter monitoring system during the study.

16. A method of acquiring data for an electrophysiological study, the method including:
 initiating an electrophysiological study with a catheter monitoring system;
 connecting a hot-swappable catheter input module (CIM) to the catheter monitoring system during the study; and
 receiving data from the CIM.

17. The method of claim 16, further including detecting the connection of the CIM.

18. The method of claim 16, further including configuring the catheter monitoring system to receive data from the CIM.

* * * * *